United States Patent [19]
Österlind et al.

[11] Patent Number: 5,951,523
[45] Date of Patent: *Sep. 14, 1999

[54] MEDICAL DEVICES

[75] Inventors: Roland J. Österlind, Hoeganaes; Ulf H. Wahlberg, Helsingborg, both of Sweden

[73] Assignee: Becton Dickinson Infusion Therapy AB, Helsingborg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/845,724

[22] Filed: Apr. 25, 1997

Related U.S. Application Data

[62] Division of application No. 08/588,644, Jan. 19, 1996, Pat. No. 5,672,160.

[30] Foreign Application Priority Data

Jan. 21, 1995 [GB] United Kingdom .................. 95012183

[51] Int. Cl.[6] ...................................................... A61M 5/32
[52] U.S. Cl. ............................................ 604/192; 604/198
[58] Field of Search ..................... 604/198, 192, 604/197, 263, 110

[56] References Cited

U.S. PATENT DOCUMENTS

| | | |
|---|---|---|
| Re. 34,223 | 4/1993 | Bonaldo . |
| 5,019,049 | 5/1991 | Haining . |
| 5,279,590 | 1/1994 | Sinko et al. . |
| 5,300,045 | 4/1994 | Plassche, Jr. . |
| 5,304,151 | 4/1994 | Kuracina ................................. 604/198 |
| 5,312,359 | 5/1994 | Wallace . |
| 5,490,841 | 2/1996 | Landis ................................. 604/192 X |
| 5,607,402 | 3/1997 | Dufresne et al. ....................... 604/263 |
| 5,643,219 | 7/1997 | Burns ..................................... 604/192 |
| 5,662,617 | 9/1997 | Odlell et al. ............................ 604/192 |

FOREIGN PATENT DOCUMENTS

| | | | |
|---|---|---|---|
| 0 554 841 A1 | 8/1993 | European Pat. Off. | ......... A61M 5/32 |
| 0 599 564 A1 | 6/1994 | European Pat. Off. | ......... A61M 5/32 |
| WO 93/08865 | 5/1993 | WIPO | ............................ A61M 25/06 |

*Primary Examiner*—Wynn Wood Coggins
*Assistant Examiner*—A. T. Nguyen

[57] ABSTRACT

A medical device includes a hollow needle for piercing the skin of a patient. Prior to use, the needle is located in a needle protected position within a housing. The needle can be moved outwardly from the needle protected position to an extended position where it is ready for use with the patient. After use, the needle is retracted back into the housing to the needle protected position. A door is positioned at the distal end of the housing and has an aperture. The door is slidable between a first position where the needle is in alignment with the aperture in the door so that the needle can pass through the aperture to be moved to its extended position and a second position where the needle does not line up with the aperture and thus the needle cannot be moved from the needle protected position to the needle extended position.

3 Claims, 4 Drawing Sheets

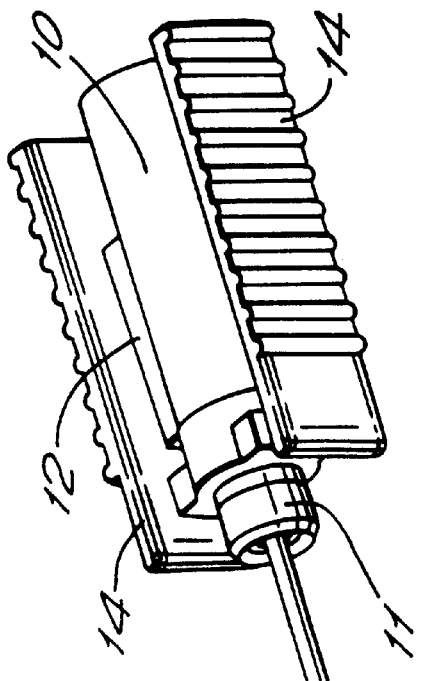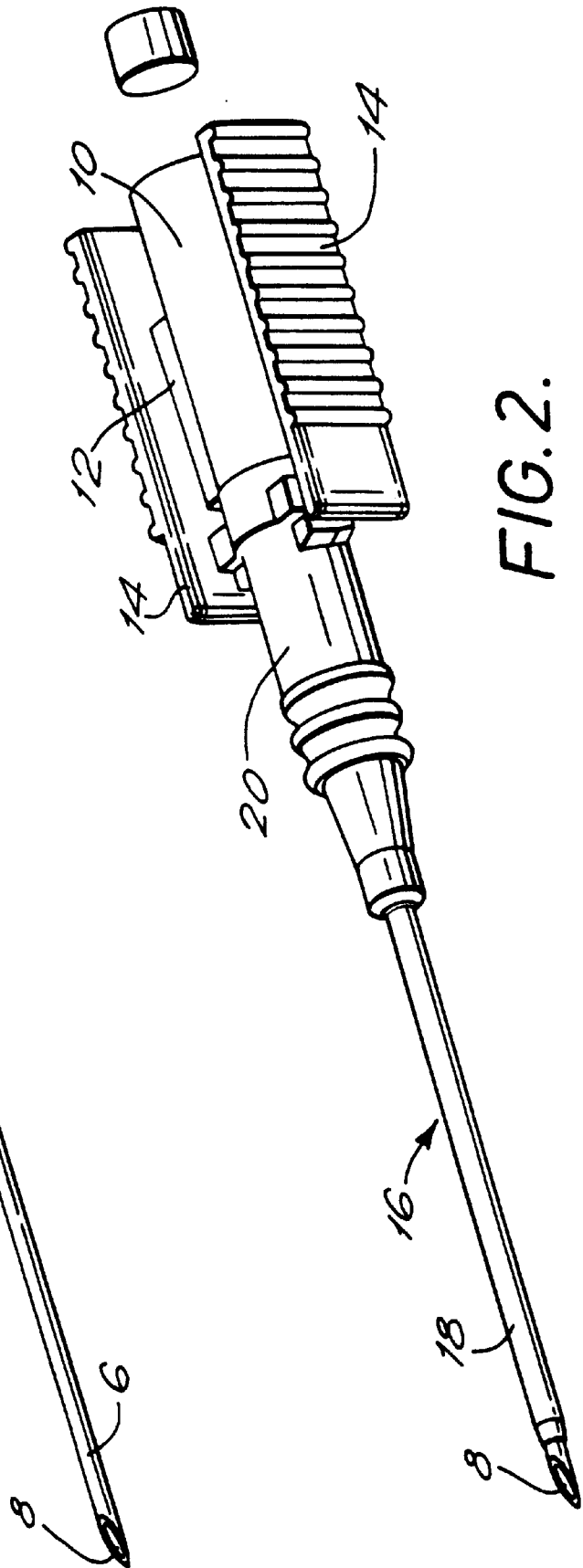

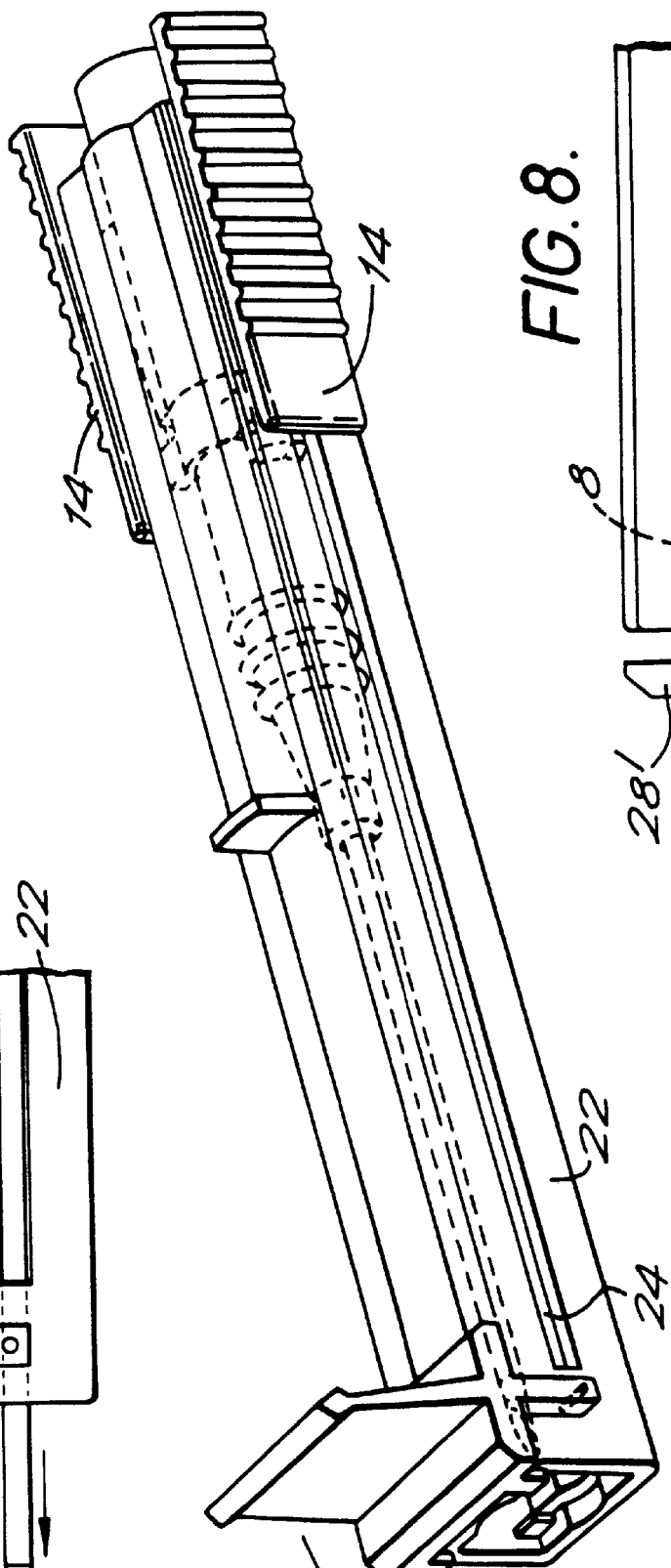

MEDICAL DEVICES

This is a division of application Ser. No. 08/588,644, filed Jan. 19, 1996 now U.S. Pat. No. 5,672,160.

The present invention relates to medical devices and in particular to medical devices such as intravenous catheters which include a hollow needle having a sharp distal end for piercing the skin of a patient.

BACKGROUND OF THE INVENTION

The existence of infectious diseases such as AIDS and Hepatitis has highlighted the danger to which medical personnel may be exposed when treating patients by means of catheter devices where a sharp needle point is used to pierce the skin of a patient. Medical personnel have been infected by physical contact with or accidental prick by an infected needle (needle-stick).

In order to protect medical personnel against inadvertent needle-stick a number of solutions have been developed whereby a protective means incorporated within the catheter prevents physical contact with the needle after use and hence against inadvertent needle-stick.

A known device for protecting a needle both before and after use is described in European Patent Publication No. 0599564, in which a needle is arranged within a housing and is displaceable between a retracted position and a second extended position. Means is provided for displacing the needle between said first and second positions. A sealing means for sealing the initially open distal end of the housing is connected to the displacing means, at least initially. The sealing means during displacement of the needle from said first retracted position to said second position, is moved in the direction towards the open distal end of the housing to a sealing position and is then fixed in said sealing position substantially sealing the interior of the housing.

The structure described in European Patent Publication 0599564 although effective to prevent inadvertent needle-stick is complicated and relatively expensive to manufacture. Furthermore, th e structure does not give any clear visible sign to show the user that the needle is locked in the protected position.

SUMMARY OF THE INVENTION

It is an aim of the present invention to provide a simple but effective means for protecting the point of a needle forming part of a medical device such as an intravenous catheter, in order to minimise the possibility of inadvertent needle-stick.

According to one aspect of the present invention, a medical device comprises a hollow needle having a sharpened distal end for piercing the skin of a patient, means for moving the needle longitudinally relative to a housing, said moving means being employed to retract the needle after use back within the housing to a needle protected position and further means located outside the housing and movable between a first position to allow longitudinally movement of the needle and a second position for preventing movement of the needle from said needle protected position.

According to a further aspect of the invention, a medical device comprises a hollow needle having a sharpened distal end for piercing the skin of a patient, the needle in a first needle protected position being located in a housing, means for moving the needle from the first position to a second position in which the sharpened distal end of the needle extends from the distal end of the housing ready for piercing the skin of a patient, said moving means being employed to retract the needle after use back within the housing to said first needle protected position and further means located outside the housing and movable between a first position to allow movement of the needle between its first and its second position and a second position for preventing movement of the needle from said first needle protected position.

In one embodiment of the invention said further means is a door mounted for sliding movement immediately adjacent the distal end of the housing between the first position in which the needle can pass from the interior of the housing and through an aperture in the door and a second position in which the door blocks the exit of the needle from the interior of the housing.

Preferably, the door includes two resilient arms which in the first position of the door engage opposite sides of the housing to latch the door in said first position.

Preferably, at least one arm has an enlarged free end which in the second position of the door engages an aperture formed in the housing adjacent its distal end.

In an alternative embodiment the door is hingedly connected to the housing immediately adjacent its distal end.

Preferably, the needle is fixedly mounted to and extends from the distal end of a body positioned within the housing, at least one web extending from the body through a slot in the housing, a gripper fixed to said web at a position outside the housing whereby the body and the needle may be moved longitudinally through the housing between said first and said second positions.

Preferably a lug is mounted for rotary movement on the proximal end of the body between the first position in which the lug can pass through the interior of the housing and a second position in which the lug is stopped from passing through the housing by said proximal end of said housing.

BRIEF DESCRIPTION OF THE DRAWINGS

Embodiments of the invention will now be described by way of example, reference being made to the Figures of the accompanying diagrammatic drawings in which:

FIG. 1 is a perspective view of a needle assembly forming part of an infusion cannula as illustrated in FIG. 3;

FIG. 2 is a perspective view similar to FIG. 1 but illustrating a catheter assembly mounted on the needle assembly of FIG. 1;

FIG. 6 is a perspective view of a second embodiment of infusion cannula;

FIG. 7 is a partial side view of the infusion cannula of FIG. 6 showing a door in a first position and;

FIG. 4 is a partial side view detail, similar to FIG. 7 but showing the door in a second position;

DESCRIPTION OF THE PREFERRED EMBODIMENT

Figure 3:
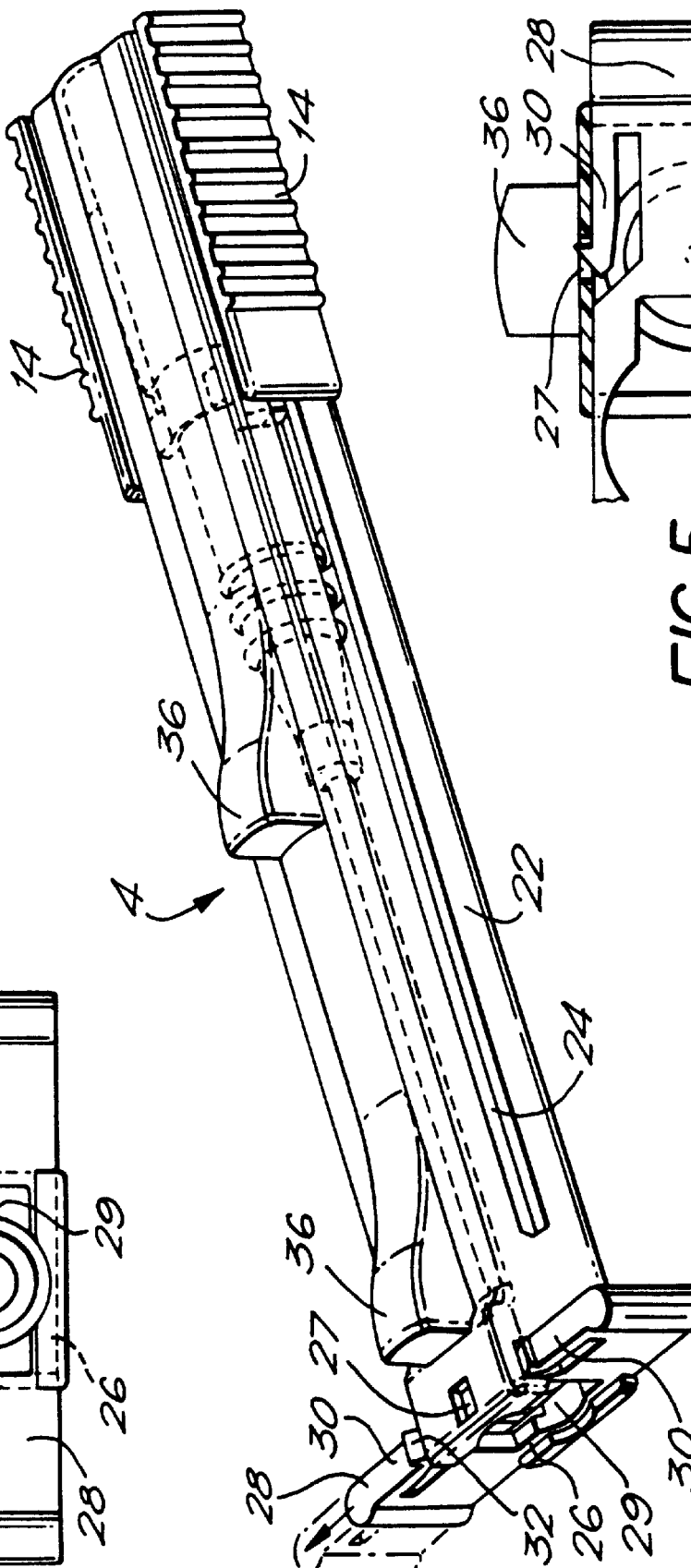
FIG. 3 is a perspective view of an infusion cannula.

As shown particularly with reference to FIG. 1, a needle assembly 2 forming part of an infusion cannula 4 (See FIG.

3) includes a hollow needle 6 having a sharpened distal end 8. The proximal end of the needle 6 is fixably mounted in a body 10 from which extends from each side thereof webs 12. As shown, each web 12 supports a serrated gripper 14. The body 10 at its distal end is formed with a boss 11.

Referring also to FIG. 2, mounted on the needle assembly 2 is a catheter assembly 16 including a hollow catheter 18 extending from a hollow catheter hub 20. Prior to use and as illustrated in FIG. 2 the needle 6 extends through the catheter hub 20 and the catheter 18 such that the sharpened distal end 8 extends outwardly from the free distal end of the catheter 18. The proximal open end of the catheter hub 20 is supported by the boss 11 of the body 10.

Referring also to FIG. 3, the sub-assembly of the needle-assembly 2 and the catheter assembly 16 is mounted in an elongate tubular housing 22 having elongate slots 24 in each side through which the webs 12 extend thereby to position each gripper 14 on the outside of the housing 22 for engagement by a nurse or doctor in a manner known per se.

The proximal end of the housing 22 may be open or closed. The distal end of the housing 22 is open and is formed at upper and lower (as shown) surfaces with a track 26 which slidably supports a door 28 having a central aperture 29. In the middle of the upper (as shown) track 26 is an aperture 27. The door 28 is provided on its upper (as shown) edge with two resilient arms 30. Each arm 30 is formed at its free end 32 with an enlarged portion which has a chamfered upper surface. In the position of the door 28 as illustrated in FIG. 4 the end 32 of each arm 30 engages co-operating sides of the housing 22 and the aperture 29 is substantially aligned with the centre of the open distal end of the housing 22.

Protuberanes 36 are formed on the upper (as shown) of the housing 22.

Figure 4:
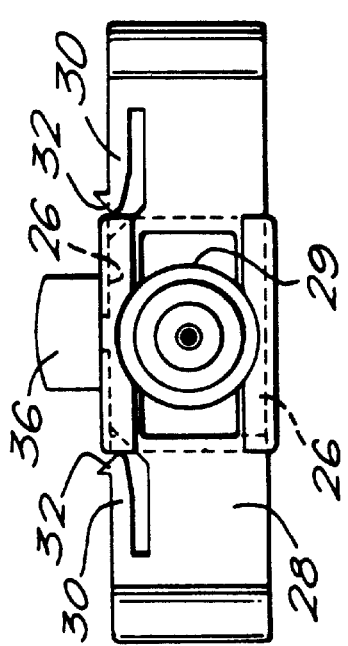
FIG. 4 is an end view of the infusion cannula illustrated in FIG. 3.

In the ready-for-use position illustrated in FIGS. 3 and 4, the sub-assembly of the needle assembly 2 and the catheter assembly 16 is located within the housing 22 with the grippers 14 located adjacent the proximal end of the housing 22 such that the sharpened distal end 8 of the needle 6 is spaced inwardly of the door 28. Further, the door 28 is positioned so that the aperture 29 is substantially central of the open distal end of the housing 22 with the champered free ends 32 of the arms 30 engaging opposite sides of the housing 22.

Figure 5:
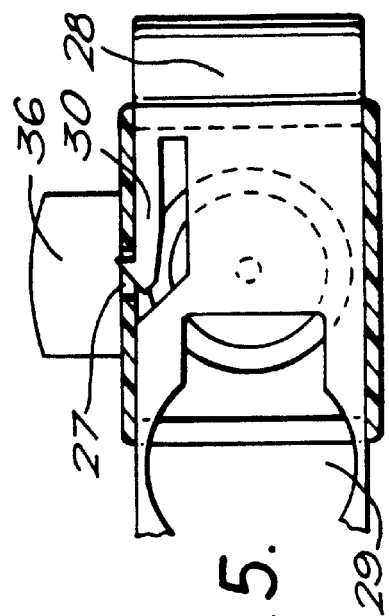
FIG. 5 is a detail partly in cross-section of the end view illustrated in FIG. 4.

To displace the needle 6 and the catheter assembly 16 from the ready-for-use position to a patient penetrating position, the grippers 14 are engaged and the sub-assembly is slid along the interior of the housing 22 in a manner known per se. Once penetration has been effected and the needle 6 withdrawn through the catheter 18 and the catheter hub 20, the grippers 14 are used to withdraw or retract the needle 6 back into the interior of the housing 22. Once the sharpened distal end 8 of the needle 6 is located within the housing 22 pressure is then applied to one side of the door 28 such that the arm 30 adjacent said one side is deflected downwardly as shown in FIGS. 4 and 5 to allow the door to slide along the tracks 26 until the enlarged chamfered end 32 engages in the aperture 27 as illustrated in FIG. 5. In this position, the open distal end of the housing 22 is shut or blocked by the door 28 and there is thus no possibility of the sharpened end 8 of the needle 6 inadvertently pricking the skin of a nurse, doctor or other user of the infusion cannula 4.

The protuberanes 36 are used in a manner known per se to assist in the relative movement of the housing 22 and the sub-assembly of the needle assembly 2 and the catheter assembly 16.

Turning now to FIGS. 6, 7 and 8 in a second embodiment of the invention in which like reference numerals denote like parts the door 28' is hingedly connected to the distal end of the housing 22. In the ready-for-use position the door 28' is in the position illustrated in FIG. 8 thereby blocking movement of the needle 6 from the interior of the housing 22. Prior to displacing the needle 6 and the catheter assembly 16 from the housing 22 from the ready-for-use position to a patient penetration position as with the previous embodiment the door 28' is moved to the position illustrated in FIGS. 6 and 7, the grippers 14 are engaged and the sub-assembly is slid through the interior of the housing 22 towards the patient penetrating position.

Once penetration has been effected, the grippers 14 are used to withdraw the needle 6 through the catheter 18 and catheter hub 20 back into the interior of the housing 22 and the door 28' is swung back again to the position illustrated in FIG. 8, thereby preventing movement of the needle 6 and in particular the sharpened distal end 8 of the needle out from the housing 22.

Figure 10:
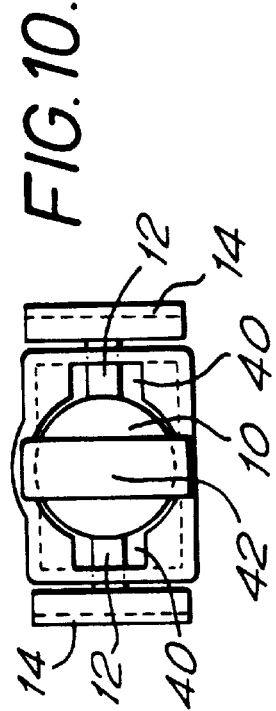
FIGS. 10 and 11 are end views of the infusion cannula of FIG. 9.
Figure 11:
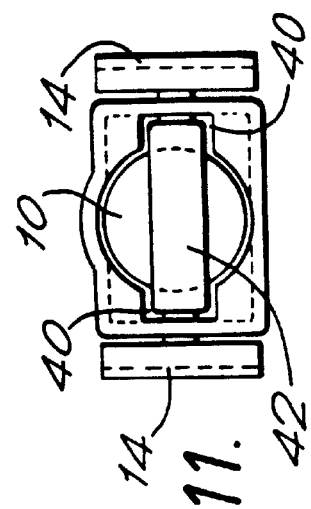
Figure 9:
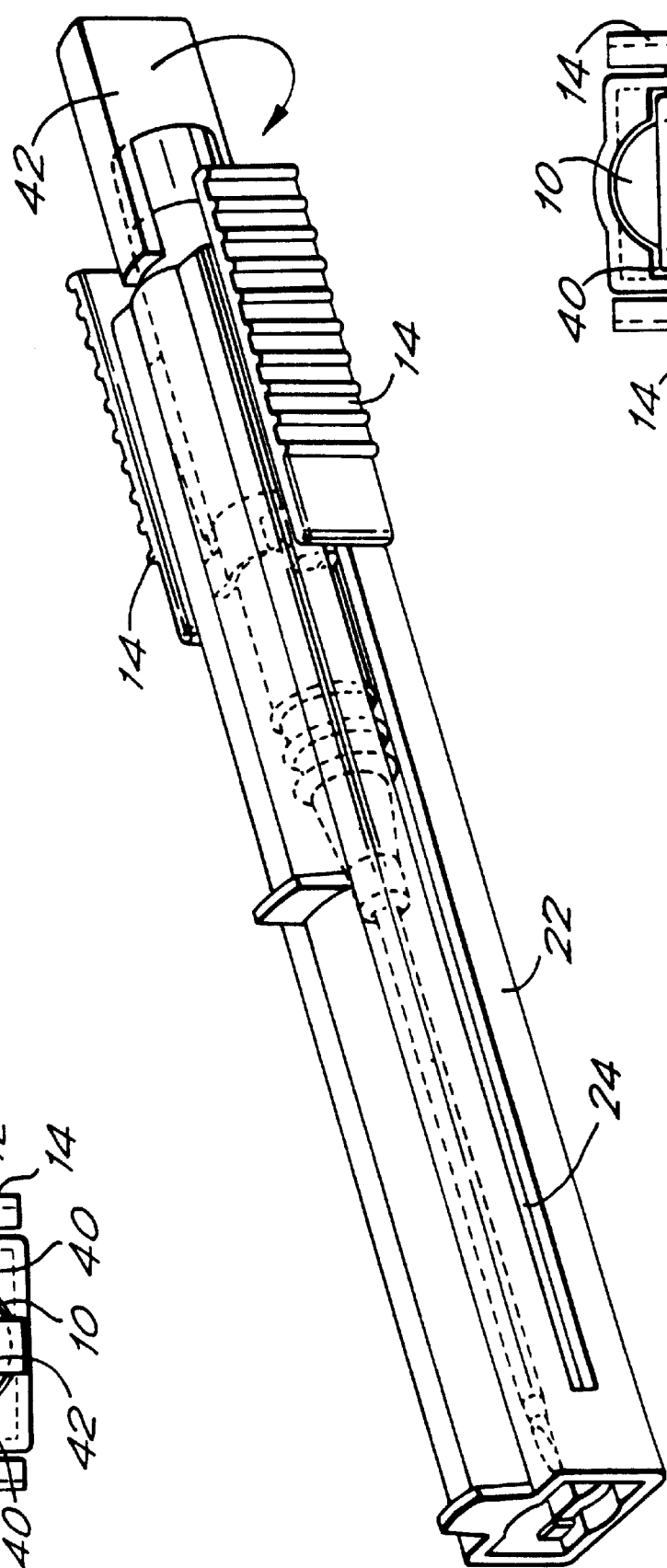
FIG. 9 is a perspective view of a further embodiment of infusion cannula.

Referring now to FIGS. 9, 10 and 11, in this embodiment of infusion cannula where like reference numerals indicate like parts the housing 22 is open both at its proximal and distal ends. However, on opposed interior surfaces of the housing 22 there are formed elongate slots which define runners 40. These runner 40 may be coincidental with the slots 24.

Mounted on the proximal end of the body 10 is a lug 42. The lug 42 is mounted for rotary movement about the longitudinal axis of the body 10 and is so shaped that in the position illustrated in FIG. 11, when the grippers 14 are pushed forward, will pass along the runners 40 thereby allowing movement of the body 10 along the interior of the housing 22.

However, when the lug 42 is moved to the position illustrated in FIGS. 9 and 10 it will be evident that it is unable to pass through the housing 22 since its forward end will butt against the proximal end of the housing 22.

In the ready-for-use position the lug 42 will be in the position illustrated in FIG. 9 and the distal end 8 of the needle 6 will be contained within the housing 22. To displace the needle 6 and the catheter assembly 16 from the ready-for-use position to a patent penetration position, the lug 42 is rotated to the position illustrated in FIG. 11, the grippers 14 are engaged and the body 10, needle 6 and the lug 42 are moved forward along the interior of the housing 22.

Once penetration has been effected the grippers 14 are used to withdraw the needle 6 through the catheter 18, catheter hub 20 and back into the interior of the housing 22. Once the sharp distal end 8 of the needle 6 is located within the housing 22 and the lug 42 extends outwardly from the proximal end of the housing 22 then the lug 42 is again rotated back to the position illustrated in FIGS. 9 and 10. This effectively stops the needle 6 from inadvertently being moved out from the safety from the interior of the housing 22.

All three embodiments described hereinbefore provide protection for the needle 6 and in particular the sharpened distal end 8 of the needle 6 before and after use. Furthermore, the various means located outside the housing for preventing movement of the needle from its retracted position within the housing substantially eliminate the possibility of accidental needle-stick in an economically effective manner.

It will be apparent that the various means for preventing accidental needle-stick are simple to manufacture and to operate.

We claim:

1. A medical device, comprising:
   a needle having a proximal end and a sharp distal tip;
   a needle hub connected to proximal end of the needle;
   a housing defining an open distal end, wherein the needle hub and needle are slidably disposed in the housing between a retracted position wherein said needle is contained within said housing and an extended position wherein said needle extends outwardly from the open distal end of said housing; and
   a door having a substantially planar surface rotatably mounted adjacent to the open distal end of the housing, wherein said door is rotatable between an open position wherein said needle can be in said extended position and a closed position wherein said door closes said open distal end of said housing to contain said needle within said housing in said retracted position and prevent said sharp distal tip of said needle from extending past the open distal end of said housing.

2. The medical device of claim 1 further comprising a means for moving the needle and needle hub between the retracted position and the extended position.

3. The medical device of claim 1 wherein the housing defines at least one longitudinally extending slot and further including a handle connected to the needle hub and extending through the slot.

* * * * *